United States Patent
Ding et al.

(10) Patent No.: US 10,679,727 B2
(45) Date of Patent: Jun. 9, 2020

(54) GENOME COMPRESSION AND DECOMPRESSION

(71) Applicant: INTERNATIONAL BUSINESS MACHINES CORPORATION, Armonk, NY (US)

(72) Inventors: Jian Dong Ding, Shanghai (CN); Min Gong, Shanghai (CN); Yun Jie Qiu, Shanghai (CN); Junchi Yan, Shanghai (CN); Ya Nan Zhang, Shanghai (CN)

(73) Assignee: International Business Machines Corporation, Armonk, NY (US)

( * ) Notice: Subject to any disclaimer, the term of this patent is extended or adjusted under 35 U.S.C. 154(b) by 611 days.

(21) Appl. No.: 15/101,946

(22) PCT Filed: Oct. 11, 2014

(86) PCT No.: PCT/CN2014/088400
§ 371 (c)(1),
(2) Date: Jun. 6, 2016

(87) PCT Pub. No.: WO2015/081754
PCT Pub. Date: Jun. 11, 2015

(65) Prior Publication Data
US 2016/0306919 A1 Oct. 20, 2016

(30) Foreign Application Priority Data

Dec. 6, 2013 (CN) .......................... 2013 1 0655168

(51) Int. Cl.
| G16B 20/00 | (2019.01) |
| G06F 16/174 | (2019.01) |
| G06F 16/22 | (2019.01) |
| G06F 16/2455 | (2019.01) |
| G16B 30/00 | (2019.01) |

(52) U.S. Cl.
CPC ......... *G16B 20/00* (2019.02); *G06F 16/1744* (2019.01); *G06F 16/2228* (2019.01); *G06F 16/2455* (2019.01); *G16B 30/00* (2019.02)

(58) Field of Classification Search
None
See application file for complete search history.

(56) References Cited

U.S. PATENT DOCUMENTS

| 8,340,914 | B2 | 12/2012 | Gatewood |
| 2009/0270277 | A1 | 10/2009 | Glick et al. |
| 2010/0169107 | A1 | 7/2010 | Ahn et al. |
| 2012/0089338 | A1 | 4/2012 | Roth |
| 2013/0132353 | A1 | 5/2013 | Mande et al. |
| 2013/0311435 | A1 | 11/2013 | Friedlander |

FOREIGN PATENT DOCUMENTS

| CN | 101914628 A | 12/2010 |
| CN | 103336916 A | 10/2013 |
| CN | 104699998 A | 6/2015 |
| KR | 1020130069427 A | 6/2013 |
| WO | 2012175245 A2 | 12/2012 |
| WO | 2015081754 A1 | 6/2015 |

OTHER PUBLICATIONS

Pruitt et al. NCBI reference sequences (RefSeq): a curated non-redundant sequence database of genomes, transcripts and proteins Nucleic Acids Research vol. 35, pp. D61-D65 (Year: 2007).*
Wang, et al., "A Novel Compression Tool for Efficient Storage of Genome Resequencing Data", Nucleic Acids Res., Jan. 25, 2011.
Wandelt, et al., "Adaptive Efficient Compression of Genomes", Algorithms for Molecular Biology, Nov. 12, 2012.
Chern, et al., "Reference Based Genome Compression", Department of Electrical Engineering Stanford University, 2012, Stanford, CA, USA.
International Search Report and Written Opinion, International Application No. PCT/CN2014/088400, International Filing Date Oct. 11, 2014.

* cited by examiner

*Primary Examiner* — John S Brusca
(74) *Attorney, Agent, or Firm* — Stephen R. Yoder; David B. Woycechowsky

(57) ABSTRACT

The present invention relates to a method and apparatus for genome compression and decompression. In one embodiment of the present invention, there is a method for genome compression, including: selecting from a reference database a reference genome that matches the genome; building an index based on positions of the reference genome's multiple segments in the reference genome; aligning the genome with the reference genome based on the multiple segments so as to identify difference data between the genome and the reference genome; and generating a compressed genome, the compressed genome including at least the index and the difference data. In other embodiments, there is provided an apparatus for genome compression. Further, there is a method and apparatus for decompressing the genome that has been compressed using the above method and apparatus.

16 Claims, 10 Drawing Sheets

612B —— CURRENT SEGMENT

610B —— TO-BE-COMPRESSED
GENOME

SCORE =

GENOME COMPRESSION AND DECOMPRESSION

CROSS-REFERENCE TO RELATED APPLICATION

This application claims priority under 35 U.S.C. § 371 from PCT Application PCT/CN2014/088400, filed on Oct. 11, 2014, which claims priority from Chinese Patent Application No. 201310655168.1 filed Dec. 6, 2013. The entire contents of both applications are incorporated herein by reference.

FIELD OF THE INVENTION

Various embodiments of the present invention relate to data compression and decompression, and more specifically, to a method and apparatus for genome compression and decompression.

BACKGROUND

With the development of biology, research on biological genes has gone deeper and deeper, e.g., into various aspects such as human health, medicine research & development, new plant and animal species and microorganism.

In short, sequencing biological genomes refers to recording a sequence of base pairs composing the chromosome of the organism. Usually the process of measuring a genome of the first sample of a species is referred to as sequencing, while the process of measuring a genome of other sample of the species is referred to as re-sequencing. A breakthrough has been achieved in sequencing and re-sequencing technologies, with various involved costs going increasingly lower. More and more individuals and/or organizations come to realize the significance of genomes, and so far genome data of a large amount of species have been obtained through sequencing/re-sequencing process.

Human genes comprise about 3 billion base pairs; according to existing representation modes, human genomes consist of about 6 billion characters (characters A, G, T and C). Therefore, storing each genome takes up much storage space. When there is a need to store a large amount of genomes or to copy and transmit genomes, there comes up a challenge regarding how to enhance the data storage/data transmission efficiency.

SUMMARY OF THE INVENTION

Biologists have found there is certain similarity among genomes of various samples of the same species. For example, the similarity among human genomes is much higher than the similarity between genomes of humans and other species.

Therefore, it is desired to develop a technical solution for compressing/decompressing a genome based on the similarity among genomes. It is desired that the technical solution can be integrated with existing genome storage modes and make full use of the similarity among genomes and further achieve efficient compression/decompression; in addition, while effectively enhancing the data compression ratio, it is further desired that decompression can be implemented with respect to only a portion of the genome rather than decompressing the entire genome.

In one embodiment of the present invention, there is provided a method for genome compression, including: selecting from a reference database a reference genome that matches the genome; building an index based on positions of the reference genome's multiple segments in the reference genome; aligning the genome with the reference genome based on the multiple segments so as to identify difference data between the genome and the reference genome; and generating a compressed genome, the compressed genome including at least the index and the difference data.

In one embodiment of the present invention, the selecting from a reference database a reference genome that matches the genome includes: selecting the reference genome based on at least one of at least one phenotypic trait characterizing reference genomes in the reference database and at least one predefined sequence in reference genomes in the reference database.

In one embodiment of the present invention, the multiple segments of the reference genome are defined based on at least one of annotation associated with the reference genome and a predefined step-length. If annotation information associated with the reference genome can be obtained, then the information is considered in preference.

In one embodiment of the present invention, there is provided a method for genome decompression, including: in response to receiving a compressed genome that has been compressed according to a method of the present invention, obtaining from a reference database a reference genome that matches the compressed genome; and decompressing, according to an index in the compressed genome, the compressed genome based on difference data between the reference genome and the compressed genome.

In one embodiment of the present invention, there is provided an apparatus for genome compression, including: a selecting module configured to select from a reference database a reference genome that matches the genome; an indexing module configured to build an index based on positions of the reference genome's multiple segments in the reference genome; an aligning module configured to align the genome with the reference genome based on the multiple segments so as to identify difference data between the genome and the reference genome; and a generating module configured to generate a compressed genome, the compressed genome including at least the index and the difference data.

In one embodiment of the present invention, the selecting module includes at least one of: a first selecting module configured to select the reference genome based on at least one phenotypic trait characterizing reference genomes in the reference database; and a second selecting module configured to select the reference genome based on at least one predefined sequence in reference genomes in the reference database.

In one embodiment of the present invention, the multiple segments of the reference genome are defined based on at least one of annotation associated with the reference genome and a predefined step-length.

In one embodiment of the present invention, there is provided an apparatus for genome decompression, including: an obtaining module configured to, in response to receiving a compressed genome that has been compressed according to a method of the present invention, obtain from a reference database a reference genome that matches the compressed genome; and a decompressing module configured to decompress, according to an index in the compressed genome, the compressed genome based on difference data between the reference genome and the compressed genome.

By means of the technical solution according to the embodiments of the present invention, a representative genome can be used as a reference genome; when storing a new to-be-processed genome, only difference between the to-be-processed genome and the reference genome is saved, thereby reducing the amount of data significantly. On the other hand, with the technical solution according to the embodiments of the present invention, where a compressed genome includes an index, any base pair in the genome can be found rapidly by querying the index, and further a gene segment desired to be accessed can be found rapidly without decompressing the entire compressed genome.

BRIEF DESCRIPTION OF SEVERAL VIEWS OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION OF THE INVENTION

Figure 1:
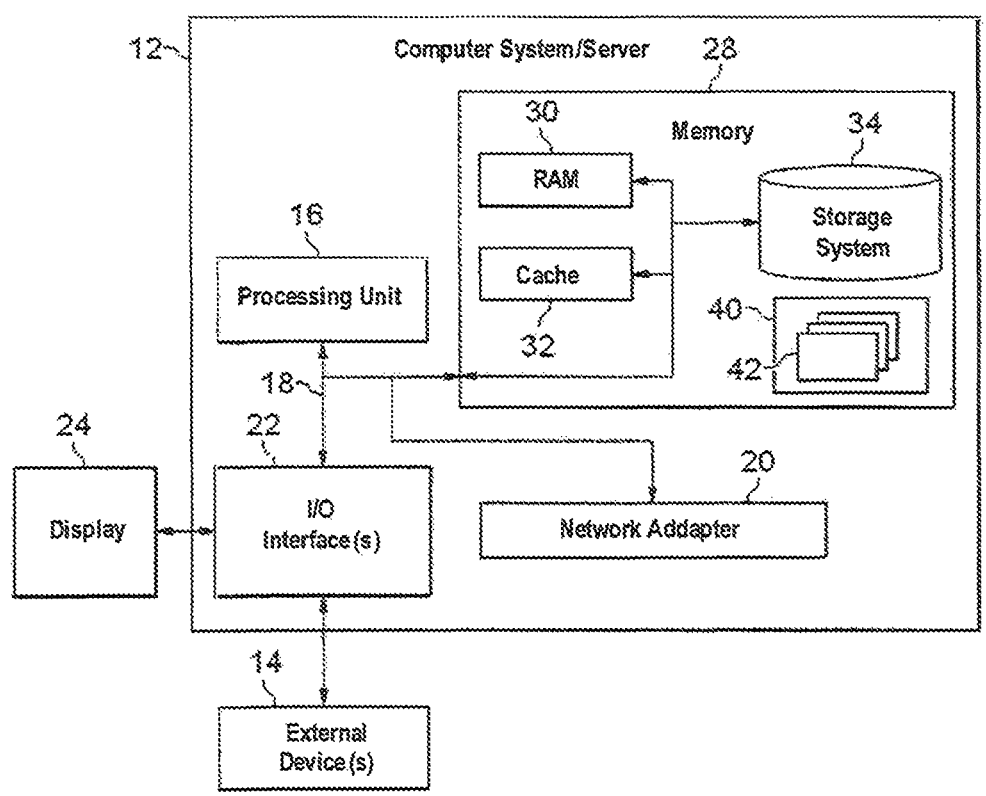
FIG. 1 schematically shows an exemplary computer system which is applicable to implement the embodiments of the present invention.

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

As will be appreciated by one skilled in the art, aspects of the present invention can be embodied as a system, method or computer program product. Accordingly, aspects of the present invention can take the form of an entirely hardware embodiment, an entirely software embodiment (including firmware, resident software, micro-code, etc.) or one embodiment combining software and hardware aspects that can all generally be referred to herein as a "circuit," "module" or "system." Furthermore, in some embodiments, aspects of the present invention can take the form of a computer program product embodied in at least one computer readable medium(s) having computer readable program code embodied thereon.

Any combination of at least one computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium can include the following: an electrical connection having at least one wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain, or store a program for use by or in connection with an instruction execution system, apparatus, or device.

A computer readable signal medium can include a propagated data signal with computer readable program code embodied therein, for example, in baseband or as part of a carrier wave. Such a propagated data signal can take any of a variety of forms, including, but not limited to, an electromagnetic signal, optical signal, or any suitable combination thereof. A computer readable signal medium can be any computer readable medium that is not a computer readable storage medium and that can communicate, propagate, or transport a program for use by or in connection with an instruction execution system, apparatus, or device.

Program code embodied on a computer readable medium can be transmitted using any appropriate medium, including but not limited to wireless, wireline, optical fiber cable, RF, etc., or any suitable combination of the foregoing.

Computer program code for carrying out operations for aspects of the present invention can be written in any combination of at least one programming languages, including an object oriented programming language such as Java, Smalltalk, C++ or the like and conventional procedural programming languages, such as the "C" programming language or similar programming languages. The program code can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer readable medium that can direct a computer, other programmable data processing apparatus, or other devices to function in a particular manner, such that the instructions stored in the computer readable medium produce an article of manufacture including instruction means which implements the function/act specified in the flowchart and/or block diagram block or blocks.

The computer program instructions can also be loaded onto a computer, other programmable data processing apparatus, or other devices to cause a series of operational steps to be performed on the computer, other programmable data processing apparatus or other devices to produce a computer implemented process such that the instructions which execute on the computer or other programmable apparatus provide processes for implementing the functions/acts specified in the flowchart and/or block diagram block or blocks.

Referring now to FIG. 1, in which a block diagram of an exemplary computer system/server 12 which is applicable to implement the embodiments of the present invention is illustrated. Computer system/server 12 illustrated in FIG. 1 is only illustrative and is not intended to suggest any limitation as to the scope of use or functionality of embodiments of the invention described herein.

As illustrated in FIG. 1, computer system/server 12 is illustrated in the form of a general-purpose computing device. The components of computer system/server 12 can include, but are not limited to, at least one processors or processing units 16, a system memory 28, and a bus 18 that couples various system components including the system memory 28 and processing units 16.

Bus 18 represents at least one of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not illustrated in FIG. 1 and typically called a "hard drive"). Although not illustrated in FIG. 1, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each drive can be connected to bus 18 by at least one data media interfaces. As will be further depicted and described below, memory 28 can include at least one program product having a set (e.g., at least one) of program modules that are configured to carry out the functions of embodiments of the present invention.

Program/utility 40, having a set (at least one) of program modules 42, can be stored in memory 28 by way of example, and not limitation, as well as an operating system, at least one application programs, other program modules, and program data. Each of the operating system, at least one application programs, other program modules, and program data or some combination thereof, can include an implementation of a networking environment. Program modules 42 generally carry out the functions and/or methodologies of embodiments of the present invention as described herein.

Computer system/server 12 can also communicate with at least one external devices 14 such as a keyboard, a pointing device, a display 24, etc.; at least one devices that enable a user to interact with computer system/server 12; and/or any devices (e.g., network card, modem, etc.) that enable computer system/server 12 to communicate with at least one other computing devices. Such communication can occur via Input/Output (I/O) interfaces 22. Still yet, computer system/server 12 can communicate with at least one networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not illustrated, other hardware and/or software components can be used in conjunction with computer system/server 12. Examples, include, but are not limited to: microcode, device drivers, redundant processing units, external disk drive arrays, RAID systems, tape drives, and data archival storage systems, etc.

Figure 2:
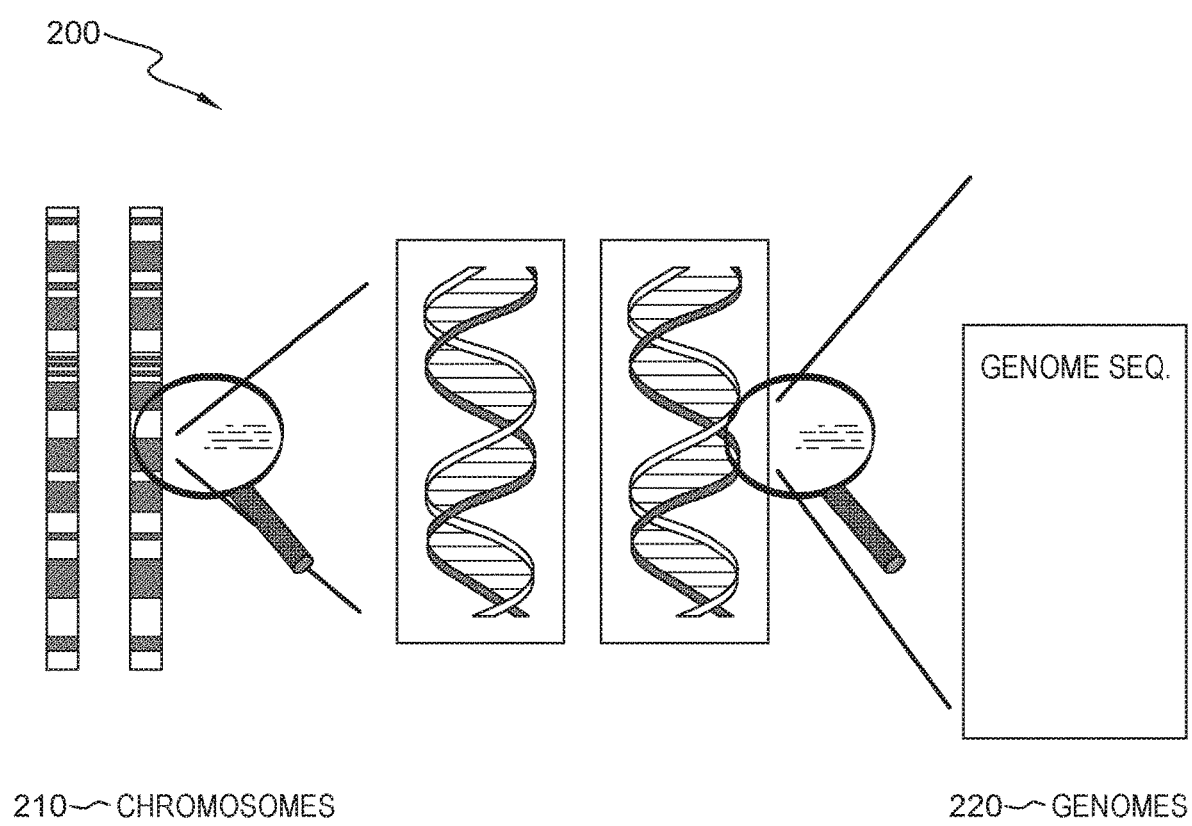
FIG. 2 schematically shows a diagram of the data structure of a hypothetical genome obtained from sequencing a hypothetical organism—this sequence(s) does not correspond to any real word species or organism and is therefore not a real genome sequence, but, rather, is set forth for pedagogical purposes and not for any biological significance.

FIG. 2 schematically shows a diagram 200 of the data structure of a genome obtained from sequencing an organism. In this figure, reference numeral 210 shows a schematic view of a chromosome, and reference numeral 220 shows a schematic view of a genome. In short, a genome of an organism can be described by accurate arrangement of base pairs of deoxyribonucleic acid (DNA). In other words, the genome can be represented by an ordered sequence constructed by A, G, T and C four bases. Genomes of different organisms have different lengths. For example, human genomes consist of about 3 billion base pairs (i.e., 6 billion characters), while genomes of other organisms can have different lengths.

Figure 3:
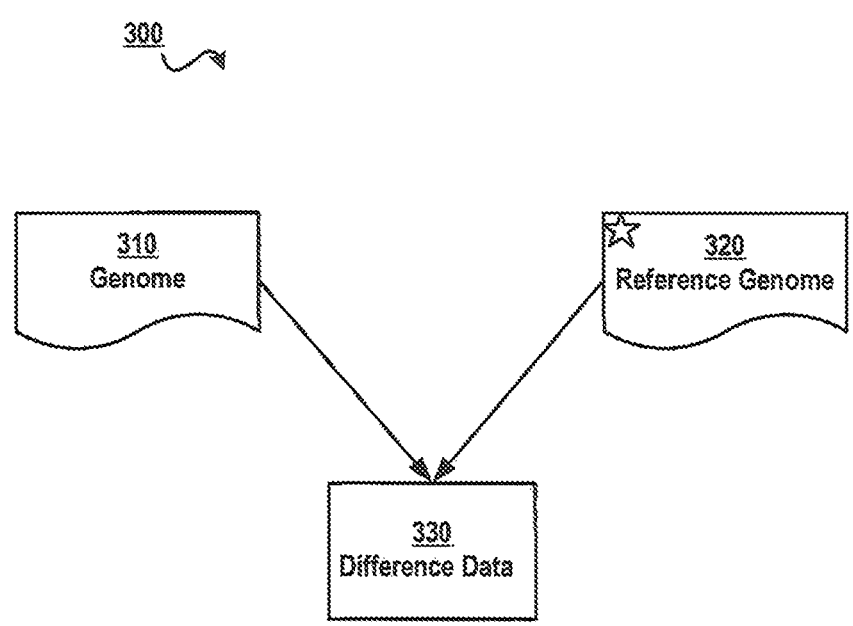
FIG. 3 schematically shows a schematic view of a method for genome compression according to one embodiment.

FIG. 3 schematically shows a schematic view 300 of a method for genome compression according to one embodiment. Currently there have been proposed methods for genome compression by looking for differences between a current genome and a reference genome. As shown in FIG. 3, a genome 310 is a to-be-compressed genome, while a reference genome 320 is a "standard genome" serving as alignment basis. An alignment can be made between the to-be-compressed genome 310 and the reference genome 320, and only difference data 330 between genome 310 and reference genome 320 are saved in a compressed genome.

With the development of network technologies, there already exist many organizations that can provide reference genomes, and these reference genomes can be accessed conveniently via networks. According to the genome compression method as shown in FIG. 3, by transmitting only difference data (e.g., difference data 330) between the genome and the reference genome during genome transmission, raw data of genome 310 can be obtained based on transmitted difference data 330 and reference genome 320 obtained from network access.

Although the above method can enhance the data compression efficiency to a given extent, there still exist the following drawbacks: on one hand, it is difficult to effectively select from multiple existing reference genomes a reference genome that best matches the to-be-compressed genome; on the other hand, difference data are compressed as a whole in order to achieve a higher compression ratio, whereas when it is desired to only access a base pair at a specific position in the genome, the raw genome must be decompressed before locating the specific base pair.

In view of these drawbacks in the above technical solution, the present invention proposes a method for genome compression. The method includes: selecting from a reference database a reference genome that matches the genome; building an index based on positions of the reference genome's multiple segments in the reference genome; aligning the genome with the reference genome based on the multiple segments so as to identify difference data between the genome and the reference genome; and generating a compressed genome, the compressed genome at least including the index and the difference data.

Figure 4:
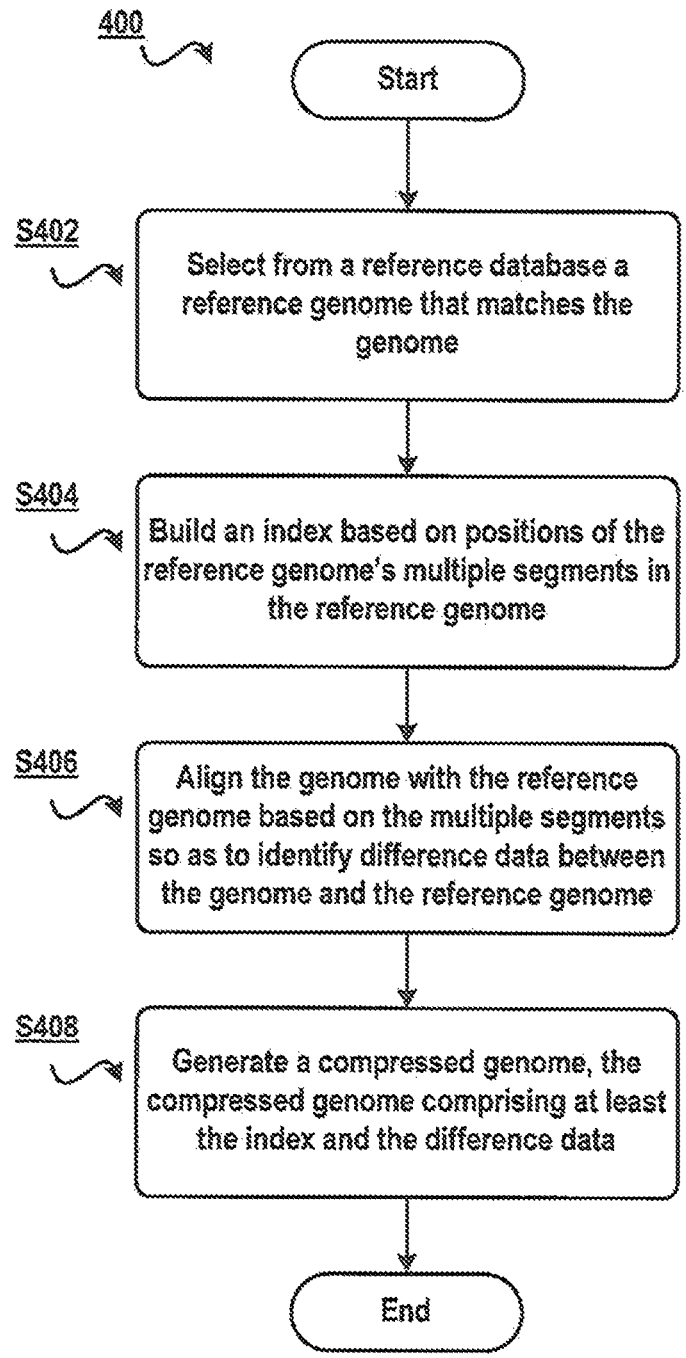
FIG. 4 schematically shows a schematic view of a method for genome compression according to one embodiment of the present invention.

FIG. 4 schematically shows a schematic view 400 of a method for genome compression according to one embodiment of the present invention. First of all, in step S402 a reference genome that matches the genome is selected from a reference database. Note multiple reference genomes are stored in the reference database here, and these reference genomes can come from multiple samples of multiple species and multiple reference genomes from various refined categories of other animal species. Since genomes of the same species have a higher similarity (i.e., text similarity among base characters in genomes), providing a reference database including abundant reference genomes helps to find a reference genome that better matches a to-be-compressed genome, so as to further enhance the data compression ratio. In the context of the present invention, "to match" represents that two genomes have a higher similarity.

In addition, the reference database mentioned in the present invention can further be enriched as new to-be-compressed genomes are processed. Detailed description will be presented below in this regard.

In step S404, an index is built based on positions of the reference genome's multiple segments in the reference genome. Since a genome usually consists of billions of characters, an index can further be built in order to locate specific positions in the genome much quickly. An index can be built according to multiple segments in the reference genome. In the context of the present invention, a segment refers to bases between the starting position and the ending position in the genome. For example, at1g33500:1-10000 represents the segment is named at1g33500, and the starting and ending positions of bases in the segment are 1 and 10000 respectively.

In the context of the present invention, for the sake of convenience, segments are defined according to biological functions of various bases in the genome, or segments are defined in other manners. Detailed description will be presented below in this regard.

In step S406, the genome is aligned with the reference genome based on the multiple segments, so as to identify difference data between the genome and the reference genome. Since a genome consists of a huge amount of bases, by taking each segment among the multiple segments as a unit, the base sequence in each segment of the reference genome is aligned with the to-be-compressed genome; when a portion that matches the segment is found in the to-be-compressed genome, only differences between the portion and a character sequence in the segment are recorded.

Finally in step S408, a compressed genome is generated, the compressed genome including at least the index and the difference data. Since the compressed genome does not include a base sequence that is the same as the reference genome, the space occupied by the compressed genome can be reduced greatly. When the reference database consists of only one reference genome, the compressed genome does not have to include an identifier of the reference genome; when the reference database consists of multiple reference genomes, the compressed genome should include identifiers of these reference genomes, so that it can be found through the identifiers which reference genome is used in compression.

In addition, new reference genomes can be added to the reference database gradually; for example, the reference database can be gradually updated during genome compression. Specifically, with respect to a newly inputted genome A, when no reference genome with a higher similarity can be found in the reference database, it can be considered that genome A can belong to a new species, and thus genome A can be added to a candidate list. When genomes in the candidate list amount to a certain number, a clustering method can be used and the most representative to-be-compressed genome obtained from clustering can be added to the reference database.

In addition, the purpose of including the index in the compressed genome lies in when there is a need to only access bases in a specific position range in the compressed genome, a portion corresponding to the specific position range can be quickly found among the difference data by the index, and then partial decompression is conducted based on the reference genome and the corresponding portion among the difference data, rather than the whole genome being decompressed and then a specified position range being found therein.

In one embodiment of the present invention, the selecting from a reference database a reference genome that matches the genome includes: selecting the reference genome based on at least one of at least one phenotypic trait characterizing reference genomes in the reference database and at least one predefined sequence in reference genomes in the reference database.

Various approaches can be used to find in a reference database a reference genome that matches the genome. Specifically, the reference database can further include additional information describing at least one phenotypic trait of each reference genome, and the phenotypic trait can include multiple aspects, such as skin color, hair color for humans. Therefore, the phenotypic trait characterizing each reference genome can be described by a multi-dimensional vector $V_{PT}=(pt1, pt2, \ldots)$. In addition, 10 levels from 1 to 10 can be set to describe colors from white to black. Therefore, the multi-dimensional vector can be represented as $V_{PT}=(2,3, \ldots)$. Phenotypic traits in the reference database can be stored in a format as shown in Table 1 below.

TABLE 1

| | Phenotypic Trait | | |
|---|---|---|---|
| Reference Genome No. | Skin Color | Hair Color | ... |
| 1 | 2 | 3 | ... |
| 2 | 3 | 9 | ... |
| ... | ... | ... | ... |

Since phenotypic traits of the to-be-compressed genome can be collected, a reference genome that is similar to the to-be-compressed genome can be selected by comparing phenotypic traits of the to-be-compressed genome and each reference genome. In one embodiment of the present invention, the selecting the reference genome includes: calculating a first similarity between the at least one phenotypic trait characterizing the genome and at least one phenotypic trait characterizing a reference genome in the reference database; and selecting the reference genome with the first similarity larger than a first threshold.

Those skilled in the art can adopt various approaches to calculating the similarity. For example, an Euclidean distance between a vector V1 describing the phenotypic trait of the to-be-compressed genome and a vector V2 describing a phenotypic trait of a reference genome in the reference database is calculated and used as the first similarity. Alternatively, if the importance of a certain phenotypic trait is considered to be higher, a higher weight can be assigned to the phenotypic trait.

The reference genome with the first similarity larger than a first threshold can be selected; or when there exist multiple reference genomes each having a similarity larger than the first threshold, then the reference genome with the higher similarity can be selected. Those skilled in the art can further adopt other approaches to selecting the reference genome.

In one embodiment of the present invention, the selecting the reference genome includes: with respect to a current reference genome in the reference database, determining a first position set of the at least one predefined sequence in the genome, and determining a second position set of the at least one predefined sequence in the current reference genome; calculating a second similarity between the first position set and the second position set; and selecting the reference genome based on the second similarity.

If it is impossible to select the reference genome based on phenotypic traits, then the reference genome can be selected based on the similarity between positions of the predefined sequence in the to-be-compressed genome and the reference genome. In the context of the present invention, the predefined sequence can be a base sequence that only exerts little impact on the division of species. For example, since humans belong to mammals, human genomes include some conserved base sequence segments that are the same as lower mammals.

Nowadays biologists have successfully identified conserved base sequence segments that are correlated to each species, by comparing the similarity between positions of these conserved base sequence segments in the to-be-compressed genome and the reference genome, a species to which the to-be-compressed genome belongs can be inferred approximately, and further it helps to select a reference genome that is more similar to the to-be-compressed genome.

For humans, suppose multiple conserved base sequence segments have been identified, positions of these conserved base sequences in various reference genomes can be stored in a structure as shown in Table 2 below.

TABLE 2

| | Conserved Base Sequence Segments | | |
|---|---|---|---|
| Reference Genome No. | Conserved Base Sequence Segment 1 | Conserved Base Sequence Segment 2 | ... |
| 1 | Position 1-1 | Position 1-2 | ... |
| 2 | Position 2-1 | Position 2-2 | ... |
| ... | ... | ... | ... |

Like the above concrete example shown with reference to phenotypic traits, positions of multiple conserved base sequence segments in one genome can be described by a vector, e.g., $V_{SM}=$(position 1, position 2, ...). A first position set (e.g., represented as a vector $V_{SM1}$) of the multiple conserved base sequence segments in the genome is determined, a second position set (e.g., represented as a vector $V_{SM2}$) of the multiple conserved base sequence segments in the reference genome is also determined, and a similarity between the two vectors is calculated whereby the reference genome is selected.

Like the above approach to selecting the reference genome based on phenotypic traits, in one embodiment of the present invention, the reference genome can be selected based on an approach to calculating an Euclidean distance or other approaches.

The accuracy of selecting the reference genome based on positions of conversed base sequence segments is yet to be improved, so first multiple reference genomes each having a similarity larger than a specific threshold can be selected from the reference database, and then the most appropriate reference genome is selected from the multiple reference genomes.

In one embodiment of the present invention, the selecting the reference genome based on the second similarity includes: adding to a candidate list a reference genome with the second similarity larger than a second threshold; and comparing the genome with each reference genome in the candidate list so as to select from the candidate list a reference genome with a minimal difference than the genome.

In one embodiment of the present invention, a Multiple Sequence Alignment (MSA) can be used to compare the to-be-compressed genome with multiple candidate reference genomes. The Multiple Sequence Alignment is an alignment of three or more biological sequences (protein, DNA, etc.). For more details of the Multiple Sequence Alignment, reference can be made to http://en.wikipedia.org/wiki/Multiple_sequence_alignment, which is not detailed in this specification.

In one embodiment of the present invention, multiple segments of the reference genome are defined based on at least one of annotation associated with the reference genome and a predefined step-length.

In addition to the above phenotypic traits and conserved base sequence segments, the reference database can further include annotation information associated with each reference genome. The annotation information mentioned here can be, for example, annotation information that describes functions of a base sequence between certain starting and ending positions. For example, suppose a base sequence between a starting position of 1 and an ending position of 10000 is correlated to human skin color, then annotation can be added with respect to the base sequence between positions 1-10000, indicating this base portion is correlated to human skin color. In addition, other types of annotation can be added to base sequences at other positions in the genome.

So far biologists have cracked definitions of some base sequences and added lots of annotations to genomes. Therefore, segments can be defined based on starting and ending positions of base sequences associated with these annotations. In addition, since annotations are added to only one part of base sequences in genomes, other part without annotation information can be divided according to a predefined step-length. For example, division can be conducted according to a unit of 1000 bases. Or other predefined step can further be set.

Figure 5:
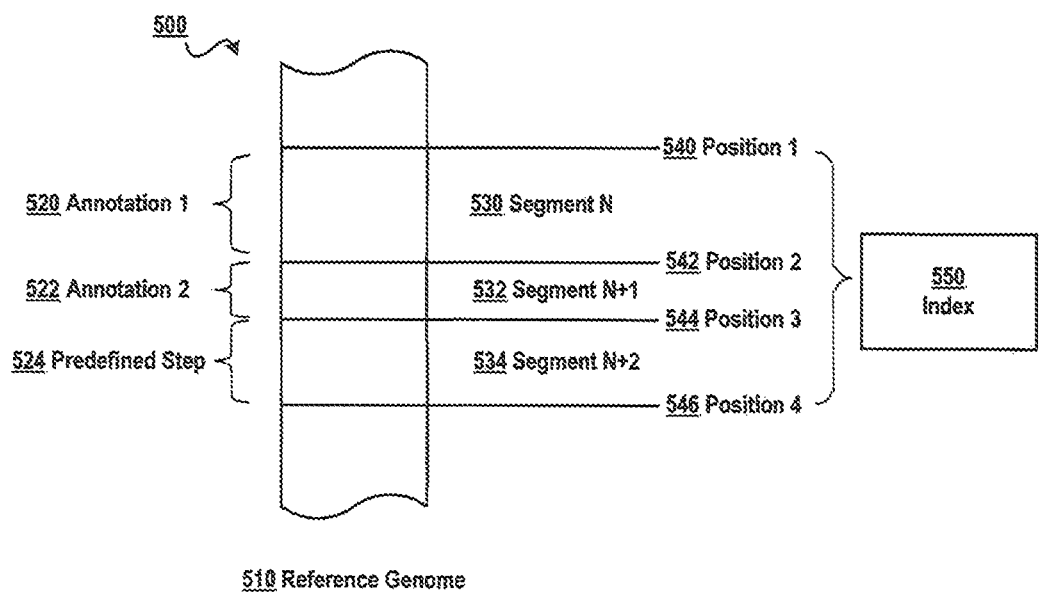
FIG. 5 schematically shows a schematic view of the process for building an index according to the embodiments of the present invention.

FIG. 5 schematically shows a schematic view 500 of the process for building an index according to one embodiment of the present invention. As shown in FIG. 6, an annotation 1 520 and an annotation 2 522 represent two annotations of a reference genome 510 in a reference database. Starting and ending positions of a base sequence corresponding to annotation 1 520 in the entire genome are position 1 540 and position 2 542, respectively. Therefore, the portion between position 1 540 and position 2 542 can act as one segment (e.g., a segment N 530). In addition, starting and ending positions of a base sequence corresponding to annotation 2 522 in the entire genome are position 2 540 and a position 3 544, respectively. Therefore, the portion between position 2 542 and position 3 544 can act as another segment (e.g., a segment N+1 532). Similarly, other portion without annotation information in reference genome 510 can further be divided into segments according to a predefined step 524, whereby a segment N+2 534 is obtained. In this manner, entire reference genome 510 can be divided into multiple segments.

In one embodiment of the present invention, one of the multiple segments in the reference genome can act as a basic unit for alignment with the to-be-compressed genome; further, one sub-segment in a segment can act as a basic unit for alignment. Alignment with a sub-segment as the basic unit possibly helps to enhance the probability of matching but also might complicate the index.

In one embodiment of the present invention, the aligning the genome with the reference genome based on the multiple segments so as to identify difference data between the genome and the reference genome includes: with respect to a sub-segment of a current segment among the multiple segments, looking up in the genome a core area that is similar to text of the sub-segment; taking text difference between the core area and the sub-segment as at least one part of the difference data; and adding to the difference data other part than the core area in the genome.

Figure 6A:
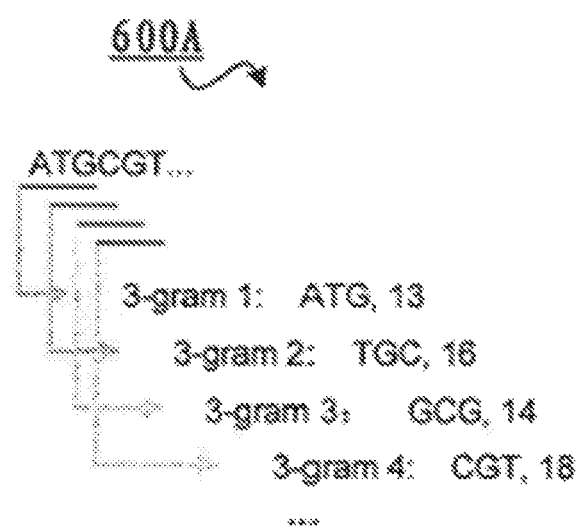
FIGS. 6A to 6C schematically show respective schematic views for identifying difference data between a hypothetical genome and a reference genome according to one embodiment of the present invention, respectively—this sequence(s) does not correspond to any real word species or organism and is therefore not a real genome sequence, but, rather, is set forth for pedagogical purposes and not for any biological significance.
Figure 6B:
Figure 6B:
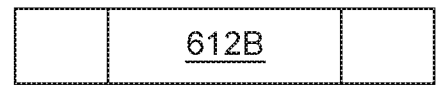
Figure 6B:
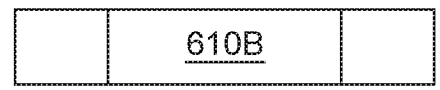
Figure 6B:
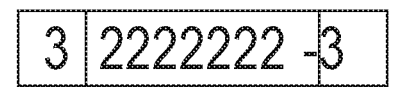
Figure 6C:
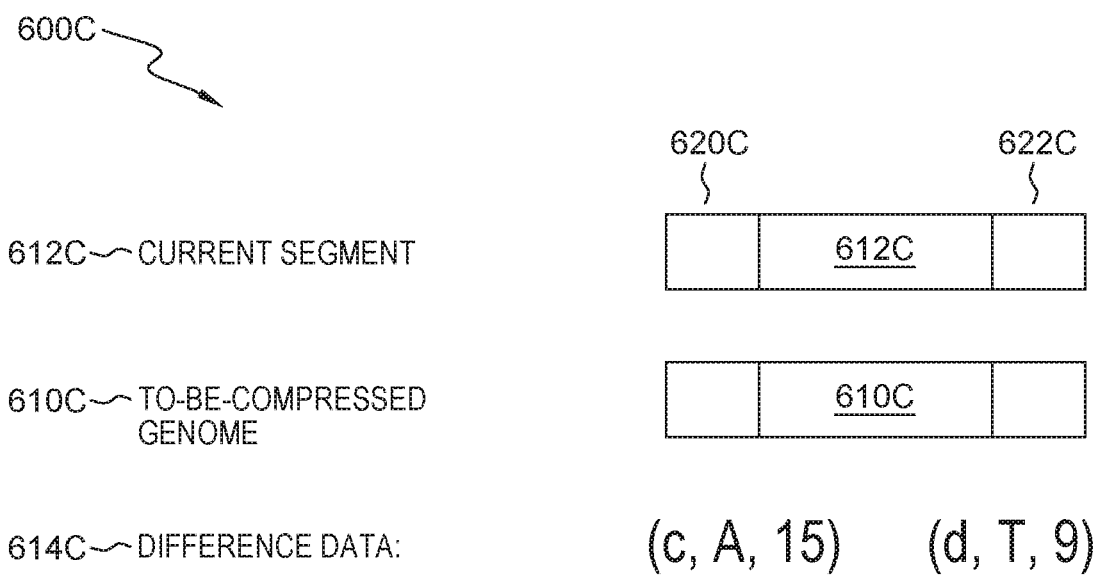

FIGS. 6A to 6C schematically show respective schematic views 600A to 600C for identifying difference data between the genome and the reference genome according to one embodiment of the present invention. Each of the multiple segments can be aligned with the to-be-compressed genome. Description is presented below to the process regarding how to align one segment with the to-be-compressed genome only.

Specifically, the comparison can be made based on an n-gram and using a sliding window. Since the genome is a character sequence consisting of A, G, T and C four bases and with billions of magnitude orders of length, an analysis can be conducted by means of n-gram in a Probabilistic Language Model. For more details of the n-gram, reference can be made to http://en.wikipedia.org/wiki/N-gram, which is not detailed in this specification.

In one embodiment of the present invention, based on a sum of scores corresponding to multiple n-grams in a current segment, an area whose sum is larger than a predefined threshold is used as the core area. Suppose a 3-gram (i.e., alignment is made with 3 bases as the basic unit) is used in one embodiment, and a score of each n-gram is calculated based on a BLOSUM matrix in this embodiment. FIG. 6A shows a score calculated with respect to each of 3-grams in a base sequence "ATGCGT . . . ." Specifically, scores of these four basic units 3-gram 1 to 3-gram 4 are 13, 16, 14 and 18, respectively.

FIG. 6B shows how to calculate a score indicating whether the to-be-compressed genome is similar to a sub-segment in the current segment. Take 3-grams for example. When scores of 3-grams in the to-be-compressed genome and in the sub-segment are the same, the total score is +2; when the scores are different, the total score is −3. By comparing a to-be-compressed genome 610B with a sub-segment in a current segment 612B in FIG. 6B, the total score=2+2+2+2+2+2+2−3+2+2+2+2+2+2+2−3+2=24. When the total score exceeds a predefined threshold, it can be considered that the base sequence in the to-be-compressed genome is a core area that is similar to text of the sub-segment.

After finding the core area that is similar to text of the sub-segment of the current segment, text difference between the core area and the sub-segment of the current segment is looked for, and the found text difference acts as one part of the difference data. Specifically, FIG. 6C shows a concrete example of the difference data. Block 620C in FIG. 6C represents the base of segment 612C and genome 610C. When block 620C of to-be-compressed genome 610C differs from that of current segment 612C the difference can be recorded as (c, A, 15), where "c" represents a change-type difference, "A" represents changing the base in the reference genome to a base "A", and the difference appears in the $15^{th}$ base.

Similarly, when a delete-type difference is present in block 622C, representing the base of current segment 612C and to-be-compressed genome 610C, it can be represented as (d, T, 9), where "d" represents a delete-type difference, "T" represents deleting a base "T," and the difference appears in the 9th base after the last difference. Similarly, those skilled in the art can further define an insert-type difference.

Note the difference data can be saved in a manner associated with the current segment. For example, the index can include an association between the difference data and the current segment, i.e., the association can represent to which segment in the reference genome the difference data corresponds. Specifically, an identifier of a segment associated with difference data can be added to the header of the difference data. For example, suppose difference data (d,T,9) shown in block 622C in FIG. 6C are associated with a segment "seg1" in the reference genome, then the difference data can be recorded as "seg1(d,T,9)". Note here given is only an example of the representation of difference data, and those skilled in the art can further use other data structure to record difference data, e.g., recording in a 4-tuple form.

In one embodiment of the present invention, when difference data correspond to a core area in a to-be-processed genome which is similar to text of a sub-segment of a current segment (i.e., difference data inside a core area), the current segment can be used as a segment associated with the difference data. In addition, when difference data are other data than various core areas in a to-be-processed genome (i.e., difference data outside core areas), a segment corresponding to a core area preceding (or following) the difference data can be used as a segment associated with the difference data. In this manner, a correspondence relationship among difference data and segments in the reference genome can be recorded explicitly. Based on the correspondence relationship and index, a specific portion in the compressed genome can be decompressed conveniently.

With the example described above, each segment (or each sub-segment of a segment) in the reference genome can be aligned with the to-be-compressed genome so as to find a corresponding core area and record text difference between each core area and a corresponding current segment (or sub-segment of a segment). For other portions than core areas in the to-be-compressed genome, it can be considered that no base sequence that is similar to these portions exists in the reference genome, so these portions can be added to the difference data directly.

In one embodiment of the present invention, with respect to the sub-segment of the current segment among the multiple segments, the core area is expanded forward and/or backward in the genome; and in response to text difference between the expanded core area and an area in the reference genome corresponding to the expanded core area being lower than a third threshold, the expanded core area is used as an expanded core area (final matching area).

Description has been presented above to how to find a core area. Alternatively, the core area can further be expanded forward and/or backward in the to-be-compressed genome. For example, the core area is expanded with one base as a step-length at a time. For example, a comparison is made as to text difference between the expanded core area and an area in the reference genome corresponding to the expanded core area; when the difference is lower than a predefined threshold, the core area is expanded. Note the expansion should not be implemented without limit but aims to enhance the compression ratio.

In one embodiment of the present invention, there is provided a method for genome decompression, including: in response to receiving a compressed genome that has been compressed according to a method of the present invention, obtaining from a reference database a reference genome that matches the compressed genome; and decompressing, according to an index in the compressed genome, the compressed genome based on difference data between the reference genome and the compressed genome.

Figure 7:
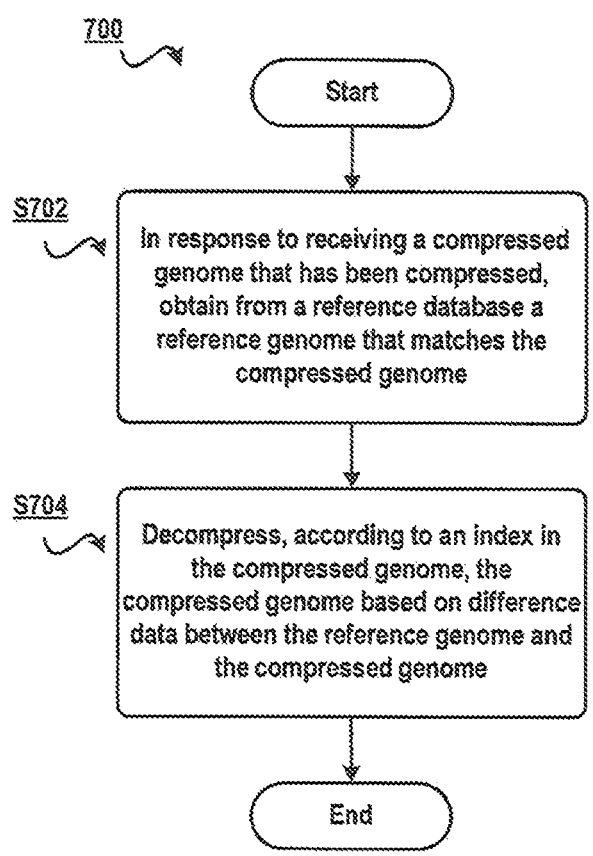
FIG. 7 schematically shows a flowchart of a method for decompressing a compressed genome according to one embodiment of the present invention.

FIG. 7 schematically shows a flowchart 700 of a method for decompressing a compressed genome according to one embodiment of the present invention. Specifically, in step S702, in response to receiving a compressed genome that has been compressed according to a method of the present invention, a reference genome that matches the compressed genome is obtained from a reference database. Since an index of the compressed genome saves information of the reference genome similar to the genome, the reference genome can be obtained via the information from the reference database.

Next in step S704, the compressed genome is decompressed, according to the index in the compressed genome, based on difference data between the reference genome and the compressed genome. In addition, since difference data in the compressed genome saves difference data between the genome and the reference genome, the difference data can be applied to the reference genome so as to restore a raw genome from the compressed genome.

In one embodiment of the present invention, there is further included: in response to a request for access to a specified portion in the compressed genome, searching for difference data corresponding to the specified portion in the difference data according to the index; and decompressing the specified portion based on the difference information and the reference genome.

As described in the above procedure for building the index, one skilled in the art can understand the index indicates respective portions in the difference data corresponds to which segment or segments in the reference genome. By this manner, a certain portion in the compressed genome can be decompressed conveniently.

Figure 8A:
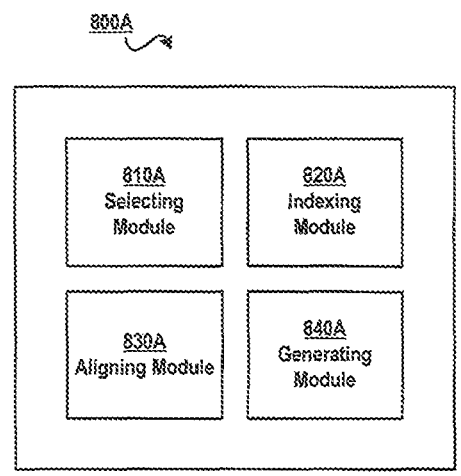
FIG. 8A schematically shows a block diagram of an apparatus for genome compression according to one embodiment of the present invention, and FIG. 8B schematically shows a block diagram of an apparatus for decompressing a compressed genome according to one embodiment of the present invention.

FIG. 8A schematically shows a block diagram 800A of an apparatus for genome compression according to one embodiment of the present invention. Specifically, there is provided an apparatus for genome compression, including: a selecting module 810A configured to select from a reference database a reference genome that matches the genome; an indexing module 820A configured to build an index based on positions of the reference genome's multiple segments in the reference genome; an aligning module 830A configured to align the genome with the reference genome based on the multiple segments so as to identify difference data between the genome and the reference genome; and a generating module 840A configured to generate a compressed genome, the compressed genome including at least the index and the difference data.

In one embodiment of the present invention, selecting module 810A includes at least one of: a first selecting module configured to select the reference genome based on at least one phenotypic trait characterizing reference genomes in the reference database; and a selecting module configured to select the reference genome based on at least one predefined sequence included in reference genomes in the reference database.

In one embodiment of the present invention, the first selecting module includes: a calculating module configured to calculate a first similarity between the at least one phenotypic trait characterizing the genome and at least one phenotypic trait characterizing a reference genome in the reference database; and a first selecting unit configured to select the reference genome with the first similarity larger than a first threshold.

In one embodiment of the present invention, the second selecting module includes: a position determining module configured to, with respect to a current reference genome in the reference database, determine a first position set of the at least one predefined sequence in the genome, and determine a second position set of the at least one predefined sequence in the current reference genome; a position similarity calculating module configured to calculate a second similarity between the first position set and the second position set; and a second selecting module configured to select the reference genome based on the second similarity.

In one embodiment of the present invention, the second selecting module includes: a candidate list generating module configured to add to a candidate list a reference genome with the second similarity larger than a second threshold; and a multiple sequence comparing module configured to compare the genome with each reference genome in the candidate list so as to select from the candidate list a reference genome with a minimal difference than the genome.

In one embodiment of the present invention, the multiple segments of the reference genome are defined based on at least one of annotation associated with the reference genome and a predefined step-length.

In one embodiment of the present invention, aligning module 830A includes: a core area generating module configured to, with respect to a sub-segment of a current segment among the multiple segments, look up in the genome a core area that is similar to text of the sub-segment; a first difference data generating module configured to take text difference between the core area and the sub-segment as at least one part of the difference data; and a second difference data generating module configured to add to the difference data other part than the core area in the genome.

In one embodiment of the present invention, the core area generating module further includes: a first expanding module configured to, with respect to the sub-segment of the current segment among the multiple segments, expand the core area forward and/or backward in the genome; and a second expanding module configured to, in response to text difference between the expanded core area and an area in the reference genome corresponding to the expanded core area being lower than a third threshold, use the expanded core area as an expanded core area.

Figure 8B:
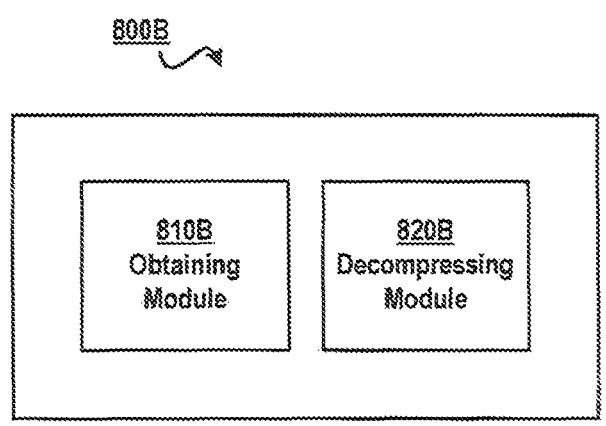

FIG. 8B schematically shows a block diagram 800B of an apparatus for decompressing a compressed genome according to one embodiment of the present invention. Specifically, there is provided an apparatus for genome decompression, including: an obtaining module 810B configured to, in response to receiving a compressed genome that has been compressed according to a method of the present invention, obtain from a reference database a reference genome that matches the compressed genome; and a decompressing module 820B configured to decompress, according to an index in the compressed genome, the compressed genome based on difference data between the reference genome and the compressed genome.

In one embodiment of the present invention, there is further comprised: a locating module configured to, in response to a request for access to a specified portion in the compressed genome, search for difference data corresponding to the specified portion in the difference data according to the index; and a partial decompressing module configured to decompress the specified portion based on the difference information and the reference genome.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks illustrated in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for compression of data representing a genome of an animal, the method comprising:
    selecting, from a reference database, a reference genome that matches the genome, with the selection including selecting the reference genome based, at least in part, on at least one phenotypic trait expressed by a plurality of genomes in the reference database, with the reference genome including multiple segments;
    building an index having a plurality of index locations respectively based on positions of the multiple segments in the reference genome;
    aligning the genome with the reference genome based on the multiple segments so as to identify difference data between the genome and the reference genome; and
    generating a compressed genome by inserting the difference data into corresponding index locations of the index.

2. The method according to claim 1, wherein selecting the reference genome includes:
    calculating a first similarity between the at least one phenotypic trait expressed by the genome and at least one phenotypic trait expressed by a reference genome in the reference database; and
    selecting the reference genome with the first similarity larger than a first threshold.

3. The method according to claim 1, wherein selecting the reference genome includes:
    determining a first position set of the at least one predefined sequence in the genome;
    determining a second position set of the at least one predefined sequence in the reference genome;
    calculating a second similarity between the first position set and the second position set; and
    selecting the reference genome based on the second similarity.

4. The method according to claim 3, wherein selecting the reference genome based on the second similarity includes:
    adding to a candidate list a reference genome with the second similarity larger than a second threshold; and
    comparing the genome with each reference genome in the candidate list so as to select from the candidate list a reference genome with a minimal difference than the genome.

5. The method according to claim 1, wherein the multiple segments of the reference genome are defined based on at least one annotation associated with the reference genome and a predefined step-length, with the step-length being a number of nucleotide bases.

6. The method according to claim 1, wherein aligning the genome with the reference genome based on the multiple segments so as to identify difference data between the genome and the reference genome includes:
    with respect to a sub-segment of a current segment among the multiple segments, looking up in the genome a core area that is similar to text of the sub-segment;

taking text difference between the core area and the sub-segment as at least one part of the difference data; and adding to the difference data other part than the core area in the genome.

7. The method according to claim 6, further includes, with respect to the sub-segment of the current segment among the multiple segments:

expanding the core area forward and/or backward in the genome; and in response to text difference between the expanded core area and an area in the reference genome corresponding to the expanded core area being lower than a third threshold, using the expanded core area as an expanded core area.

8. The method of claim 1 wherein the genome is a mammalian genome.

9. An apparatus for compression of data representing a genome of an animal, the apparatus comprising:

a selecting module configured to select from a reference database a reference genome that matches the genome, with the selecting module including at least one of: (i) a first selecting module configured to select the reference genome based on at least one phenotypic trait characterizing reference genomes in the reference database; and (ii) a second selecting module configured to select the reference genome based on at least one predefined sequence included in reference genomes in the reference database;

an indexing module configured to build an index having a plurality of index locations respectively based on positions of the multiple segments in the reference genome;

an aligning module configured to align the genome with the reference genome based on the multiple segments so as to identify difference data between the genome and the reference genome; and a generating module configured to generate a compressed genome by inserting the difference data into corresponding index locations of the index.

10. The apparatus according to claim 9, wherein the first selecting module includes:

a calculating module configured to calculate a first similarity between the at least one phenotypic trait expressed by the genome and at least one phenotypic trait expressed by a reference genome in the reference database; and a first selecting unit configured to select the reference genome with the first similarity larger than a first threshold.

11. The apparatus according to claim 9, wherein the second selecting module includes:

a position determining module configured to, with respect to the reference genome in the reference database, determine a first position set of the at least one predefined sequence in the genome, and determine a second position set of the at least one predefined sequence in the current reference genome;

a position similarity calculating module configured to calculate a second similarity between the first position set and the second position set; and a second selecting module configured to select the reference genome based on the second similarity.

12. The apparatus according to claim 11, wherein the second selecting module includes:

a candidate list generating module configured to add to a candidate list a reference genome with the second similarity larger than a second threshold; and a multiple sequence comparing module configured to compare the genome with each reference genome in the candidate list so as to select from the candidate list a reference genome with a minimal difference than the genome.

13. The apparatus according to claim 9, wherein the multiple segments of the reference genome are defined based on at least one of annotation associated with the reference genome and a predefined step-length, with the step-length being a number of nucleotide bases.

14. The apparatus according to claim 9, wherein the aligning module includes:

a core area generating module configured to, with respect to a sub-segment of a current segment among the multiple segments, look up in the genome a core area that is similar to text of the sub-segment;

a first difference data generating module configured to take text difference between the core area and the sub-segment as at least one part of the difference data; and a second difference data generating module configured to add to the difference data other part than the core area in the genome.

15. The apparatus according to claim 14, wherein the core area generating module further includes:

a first expanding module configured to, with respect to the sub-segment of the current segment among the multiple segments, expand the core area forward and/or backward in the genome; and a second expanding module configured to, in response to text difference between the expanded core area and an area in the reference genome corresponding to the expanded core area being lower than a third threshold, use the expanded core area as an expanded core area.

16. The apparatus of claim 9 wherein the genome is a mammalian genome.

* * * * *